(12) United States Patent
Al-Anzi

(10) Patent No.: US 12,300,116 B1
(45) Date of Patent: May 13, 2025

(54) BRINE DISPENSER FOR BRINE DISPENSING EXPERIMENTS UTILIZING MULTI-PLUNGING LIQUID JET REACTORS

(71) Applicant: KUWAIT UNIVERSITY, Safat (KW)

(72) Inventor: Bader Shafaqa Al-Anzi, Safat (KW)

(73) Assignee: KUWAIT UNIVERSITY, Safat (KW)

( * ) Notice: Subject to any disclaimer, the term of this patent is extended or adjusted under 35 U.S.C. 154(b) by 0 days.

(21) Appl. No.: 18/907,963

(22) Filed: Oct. 7, 2024

(51) Int. Cl.
*G09B 23/24* (2006.01)
*G01N 33/18* (2006.01)

(52) U.S. Cl.
CPC .............. *G09B 23/24* (2013.01); *G01N 33/18* (2013.01)

(58) Field of Classification Search
CPC ................................ G09B 23/00; G09B 23/24
USPC .................................................. 434/276, 298
See application file for complete search history.

(56) References Cited

U.S. PATENT DOCUMENTS

| | | | |
|---|---|---|---|
| 7,476,320 B1 | 1/2009 | Koons | |
| 8,043,094 B2* | 10/2011 | Bahler | G09B 23/12 434/150 |
| 8,668,187 B2* | 3/2014 | Al-Anzi | B01F 23/2323 261/126 |
| 9,095,826 B2* | 8/2015 | Kaya | B01F 25/211 |
| 10,125,039 B2* | 11/2018 | Al-Anzi | B01D 3/065 |
| 10,712,248 B2* | 7/2020 | Al-Anzi | B01F 23/23231 |
| 11,396,469 B2 | 7/2022 | Al-Anzi | |
| 11,406,947 B2 | 8/2022 | Ruybal et al. | |
| 11,649,624 B1* | 5/2023 | Al-Anzi | E03F 1/001 138/39 |
| 11,898,580 B2* | 2/2024 | Al-Anzi | B01F 23/23413 |
| 2017/0144910 A1* | 5/2017 | Al-Anzi | B01F 25/53 |
| 2020/0330934 A1 | 10/2020 | Al-Anzi | |
| 2022/0127165 A1 | 4/2022 | Jiang et al. | |
| 2022/0176327 A1 | 6/2022 | Al-Anzi | |

OTHER PUBLICATIONS

Al-Anzi, "Effect Of Primary Variables On A Confined Plunging Liquid Jet Reactor," Multidisciplinary Digital Publishing Institute Journal, Mar. 10, 2020, pp. 1-13.

Shrivastava, "Confined Plunging Liquid Jets For Dilution Of Brine From Desalination Plants," Multidisciplinary Digital Publishing Institute Journal, May 13, 2021, pp. 1-14.

* cited by examiner

*Primary Examiner* — Kurt Fernstrom
(74) *Attorney, Agent, or Firm* — Nath, Goldberg & Meyer; Joshua B. Goldberg

(57) ABSTRACT

A Confined Plunging Liquid Jet Reactor (CPLJR) is used for determining the effect of discharge of an effluent into seawater. A tank is provided and a plurality of water injectors supply sample effluents into the tank at multiple locations, using a pump to provide the supplied effluents. A water movement generator is used to simulate environmental movement of water in the tank, and soap bubble measurement meters/sensors are used to measure bubbles in the supplied effluents supplied by at least a subset of the water injectors, with respective ones of the bubble measurement sensors sensing bubbles associated with individual ones of the subset of water injectors. Dye injection and bubble sensors are used to observe and measure flow of injected effluent. A plurality of oxygen sensors are used for measuring oxygenation at different locations or levels in the tank.

14 Claims, 10 Drawing Sheets

BRINE DISPENSER FOR BRINE DISPENSING EXPERIMENTS UTILIZING MULTI-PLUNGING LIQUID JET REACTORS

BACKGROUND

Technical Field

The present disclosure relates to brine dispenser technology used for analysis of brine flow in simulated seawater environments, useful for analysis of brine discharge into shallow receiving waters.

Background Art

Reverse osmosis and other water treatment often involve discharge of brine into seawater environments. By way of example, discharge may be into shallow receiving waters, such as found in some parts of the Arabian Gulf, such as the typical bathymetric of the Arabian Gulf near Kuwait. In such circumstances, it is advantageous to provide multiple release ports in order to maintain better oxygenation and mixing for a broader area of seafloor.

SUMMARY

There is a need for a technique to model and develop construction designs for water treatment plants having multiple release ports. Moreover, existing modeling does not take into account the water current in the environment. It is a further desire to model an environment which considers the effect of water currents and the bathymetric characteristics, such as those of shallow receiving waters.

A Confined Plunging Liquid Jet Reactor (CPLJR) is used for determining the effect of discharge of an effluent into seawater. A tank is provided and a plurality of water injectors supply sample effluents into the tank at multiple locations, using a pump to provide the supplied effluents. A water movement generator is used to simulate environmental movement of water in the tank, and bubble measurement meters/sensors are used to measure the entrained gas/air from the ambient. The entrained air is broken into bubbles when the water jet impinges onto the receiving pool of water inside the tank, in the supplied effluents supplied by at least a subset of the water injectors, with respective bubble meters (as measurement sensors) measuring bubbles associated with individual subsets of water injectors. A plurality of oxygen sensors measure oxygenation at different locations or levels in the tank.

In one particular configuration, the tank and water injectors have a configuration for simulation of brine injection into seawater. In a further configuration, the water injectors include a plurality of downcomers, which operate as diffusers. Injection supply lines terminate at nozzles positioned to inject water into respective downcomers, with respective soap bubble meters/sensors located upstream of the nozzles.

In a further configuration, a dye injecting system, including dye injection units capable of introducing dye, is provided for at least a subset of the nozzles. Bubble meters are associated with the bubble sensors to measure entrained air upstream of the nozzles, and to measure entrained air or gas in the liquid, utilizing a surface tension enhancement substance. In one configuration, the number of automated bubble meters match the number of diffusers. Soap bubble traps are located downstream of the respective bubble meters and upstream of the respective nozzles to trap the bubble that is used to measure the entrained air.

BRIEF DESCRIPTION OF THE DRAWINGS

FIG. 1A is a single jet CPLJR and FIG. 1B is a multi-jet CPLJR multi-port diffuser.

FIGS. 2A-F are diagrams and depictions of the multi jet CPLJR of FIG. 1B. FIG. 2A is a schematic diagram of the CPLJR. FIGS. 2B and 2C are front and end views, respectively.

FIGS. 2D and 2E are oblique top and oblique rear views, respectively. FIG. 2F shows details of soap bubble meters/sensors.

DETAILED DESCRIPTION

Overview

Figure 1:
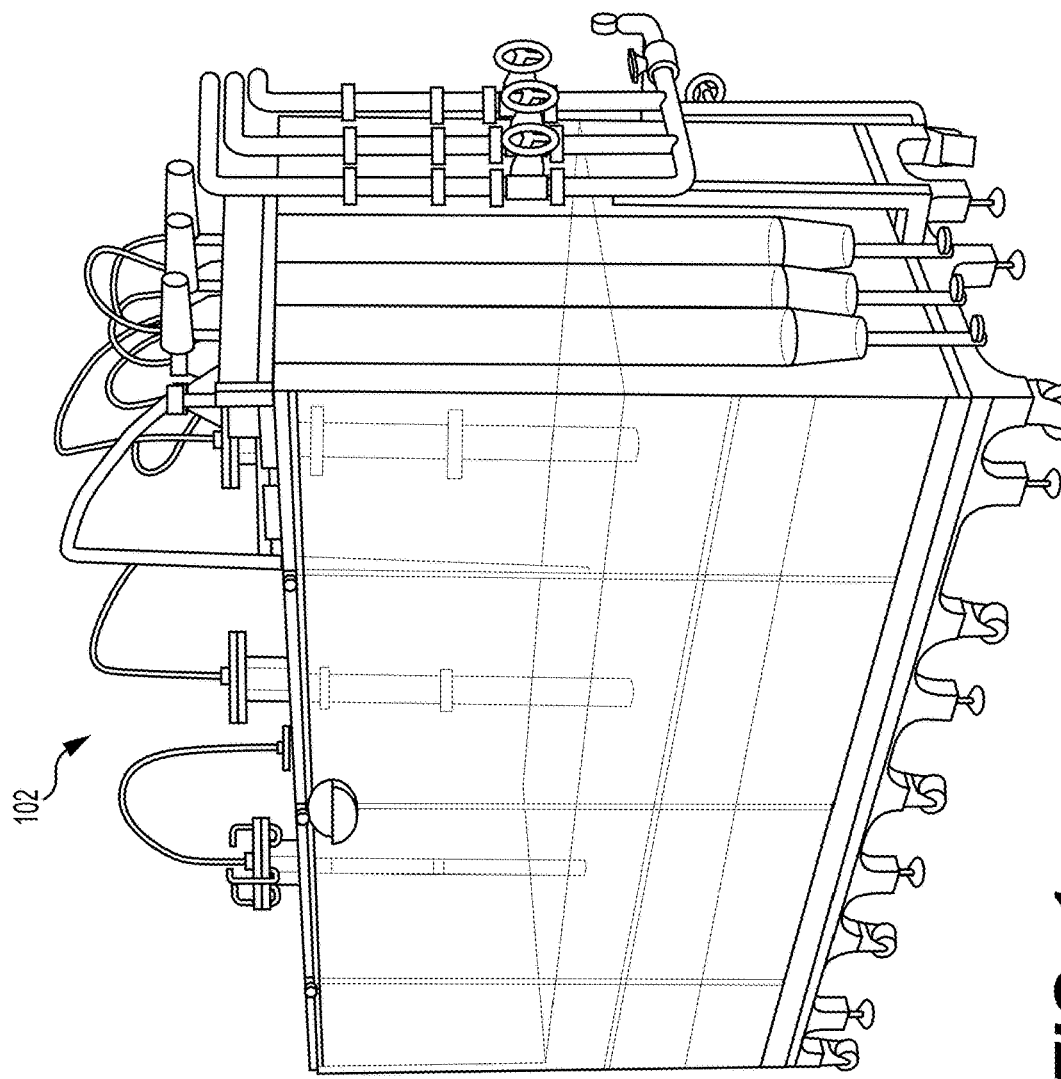
FIGS. 1A and 1B are schematic diagrams showing a pilot apparatus of a Confined Plunging Liquid Jet Reactor (CPLJR).
Figure 1:
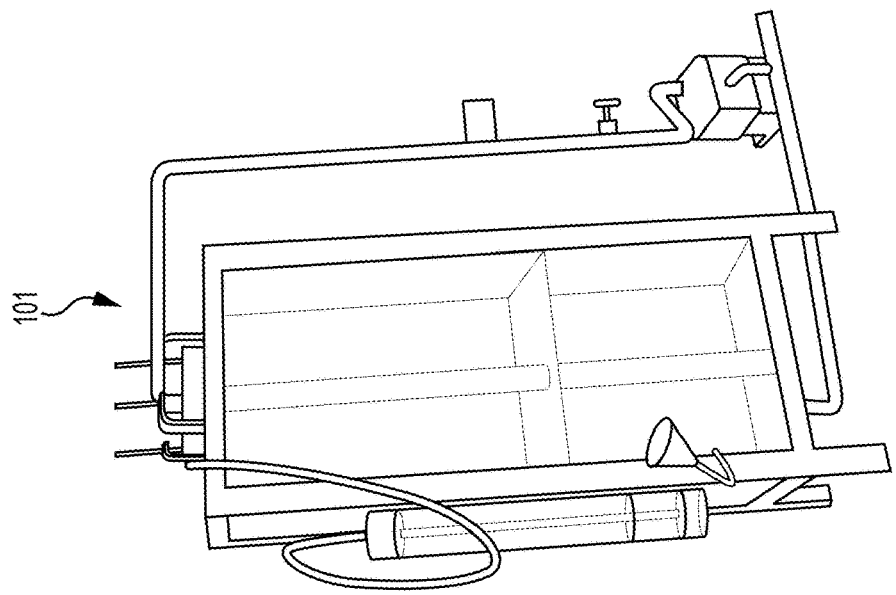

The disclosed technology provide a technique to explore the behavior of a plunging jet resulting from a single release (either unconfined or confined) of brine effluent impinging on a limited receiving pool of different concentration from that of the incoming jet. The technique provides for simulation or design considerations that take into account environmental factors such as the typical bathymetric of the Arabian Gulf near Kuwait.

This multi-jet plunging liquid jet reactor is a reactor system to employ multiple parameters for a comparative study. This reactor could also be used to compare the aeration capabilities of multi jets in comparison to a single jet with different designs.

The disclosed technique uses a confined plunging liquid jet reactor (CPLJR) with a multi-port diffuser including three bubble traps placed next to each bubble meter to trap soap bubbles. Four conductivity meters and two oxygen sensors are connected to an analyzer for accurate measurements. A wave maker is used to simulate wave activity of seawater and the influence the effect of these waves on the system performance of the multi-jet array. A dye injector injects dye into the jet flow to provide for a visual indication of the jets dispersal within the body of seawater.

In the described implementation, automated bubble meters are used. Bubble meters are used to measure the entrained air/gas from the ambient surroundings (or any source) going into the liquid, utilizing soap bubbles. The bubble meters are used to measure the entrained air/gas from the ambient surrounding (or any source) going into the liquid utilizing a surface tension enhancement substance such as a substance to produce soap bubbles. Bubble meters are used for at least a subset of the PJLRs. In one non-limiting configuration, the number of automated bubble meters match the number of diffusers. The measurement of the bubbles are achieved in a reliable and consistent fashion by the use of automated bubble meters for the respective PJLRs.

Bubble traps are used in the implementation of the disclosed technique. Bubble traps are distinct from the bubble meters, and a bubble trap is typically located downstream the bubble meter and upstream the nozzle to trap soap bubbles that are used to measure the entrained air. This prevents the bubble soap from mixing with the liquid entering the tank.

The multi-port diffuser is implemented as a multiply Confined Plunging Liquid Jet Reactor (CPLJR) or as a multiple Unconfined Plunging Liquid Jet Reactor (UCPLJR). Thus, the port diffusers are each a CPLJR or UCPLJR, which means that the apparatus can also have multiple CPLJRs of UCPLJRs as an array.

The simulation and design can be first carried out in the laboratory for a wide range of operating conditions before deploying it on-site. The technique provides a sample distance between the ports of a plunging brine jet from each other in a manner so as to achieve high dilution and dissolved oxygen (DO) concentration. More precise guidance on distancing the jets may be gained through laboratory tests according to the disclosed technique, with multi-port releases. The laboratory configuration can be scaled-up as either a pilot apparatus or part of a full-scale plant.

EXAMPLES

FIGS. 1A and 1B are schematic diagrams showing a pilot apparatus of a Confined Plunging Liquid Jet Reactor (CPLJR). FIG. 1A is a single jet CPLJR 101 and FIG. 1B is a multi-jet CPLJR multi-port diffuser 102. CLPLR units 101, 102 are used to demonstrate the differences that can be obtained between the single jet CPLJR 101 (FIG. 1A) and the multi-jet CPLJR 102 (FIG. 1B). The depicted configuration is that of a prototype pilot scale for more realistic measurements that are close to that of an actual on-site run intended to be installed at the outfall of a desalination plant in Kuwait.

The simulation and design can be first carried out in a laboratory for a wide range of operating conditions before deployment on-site. The technique provides a sample distance between the ports of a plunging brine jet from each other in a manner so as to achieve high dilution and dissolved oxygen (DO) concentration. More precise guidance on distancing the jets may be gained through laboratory tests according to the disclosed technique, with multi-port releases.

While three port diffusers or PLJRs (CPLJR or UCPLJR) are shown in FIG. 1B, the number of port diffusers is not limited to three. The number can be more or fewer than three as required by the area of outfall.

Figure 2A:
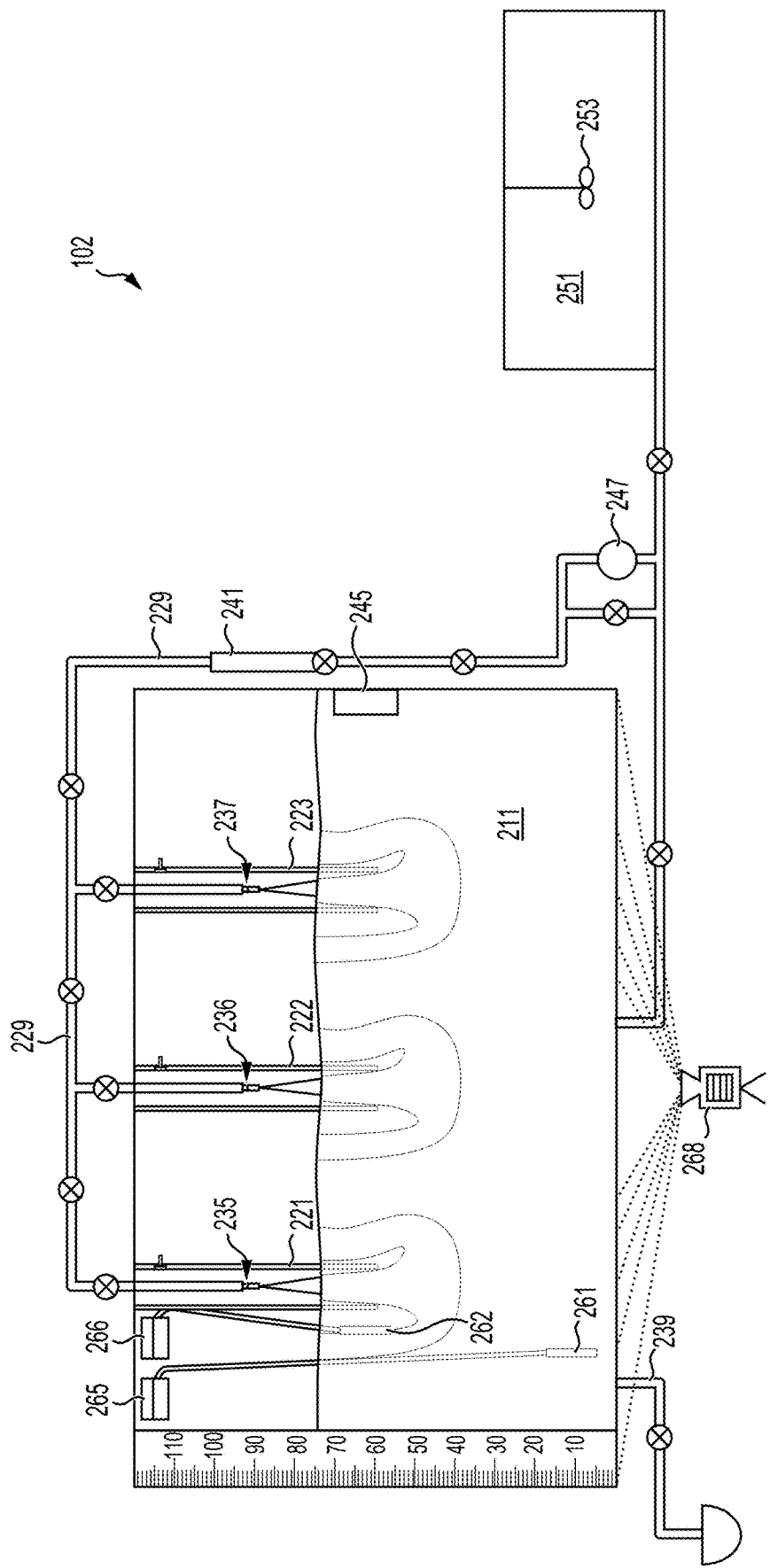
Figure 2C:
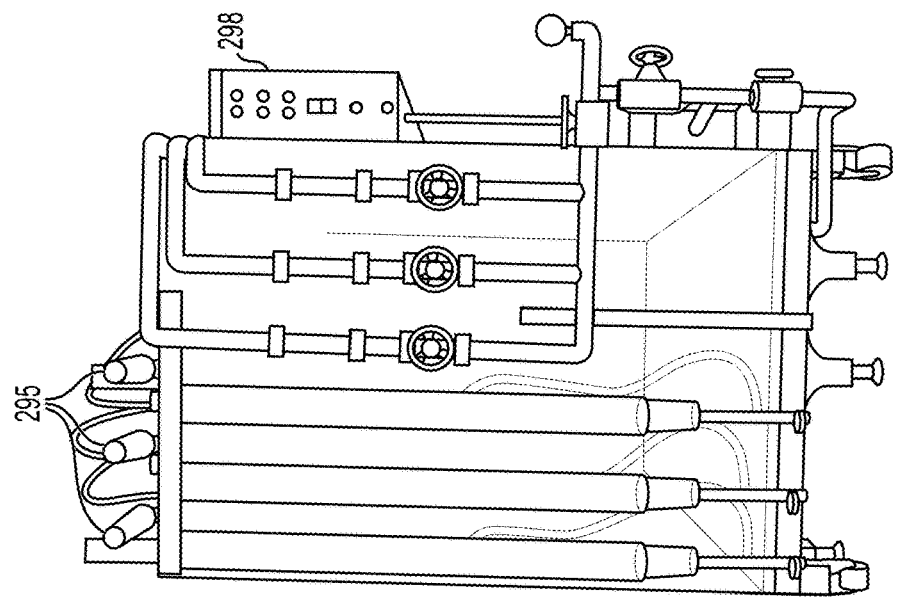
Figure 2B:
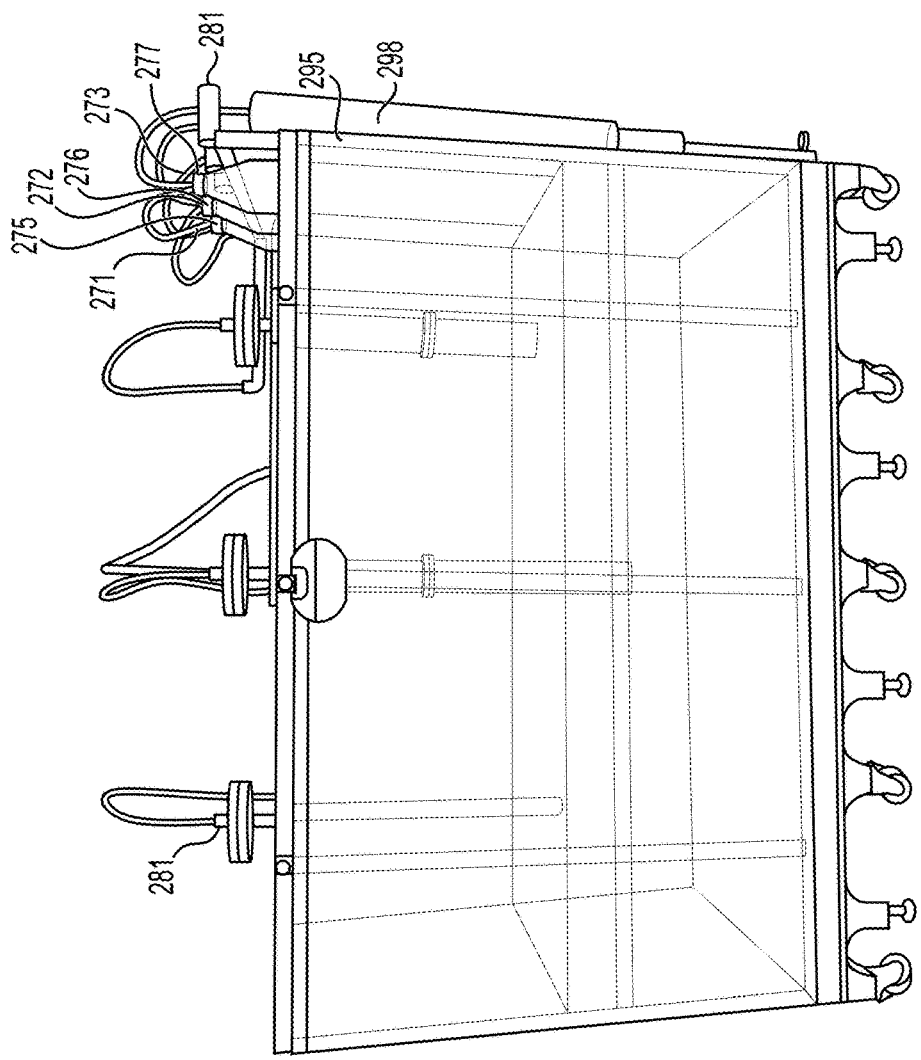
Figure 2D:
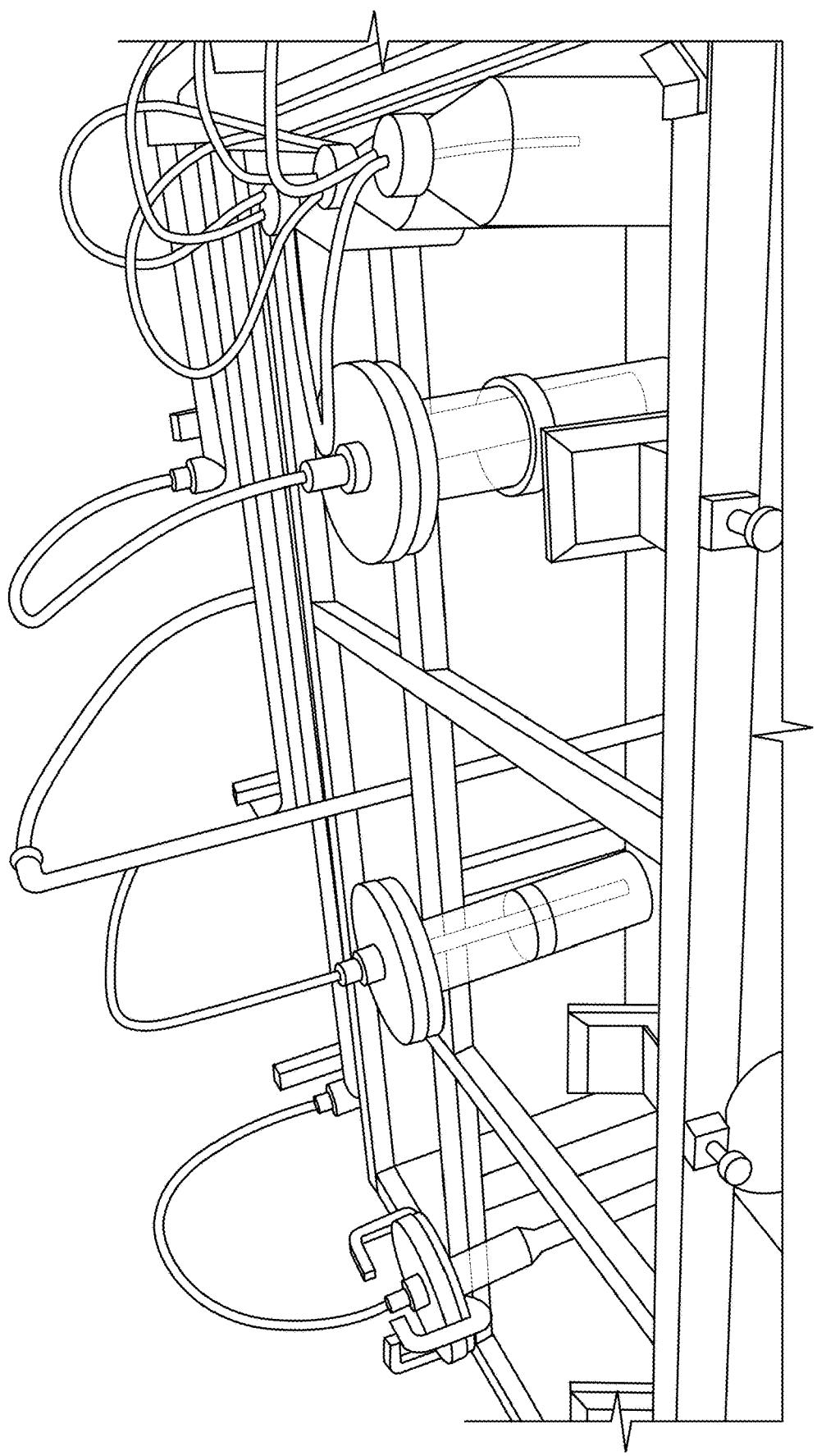
Figure 2E:
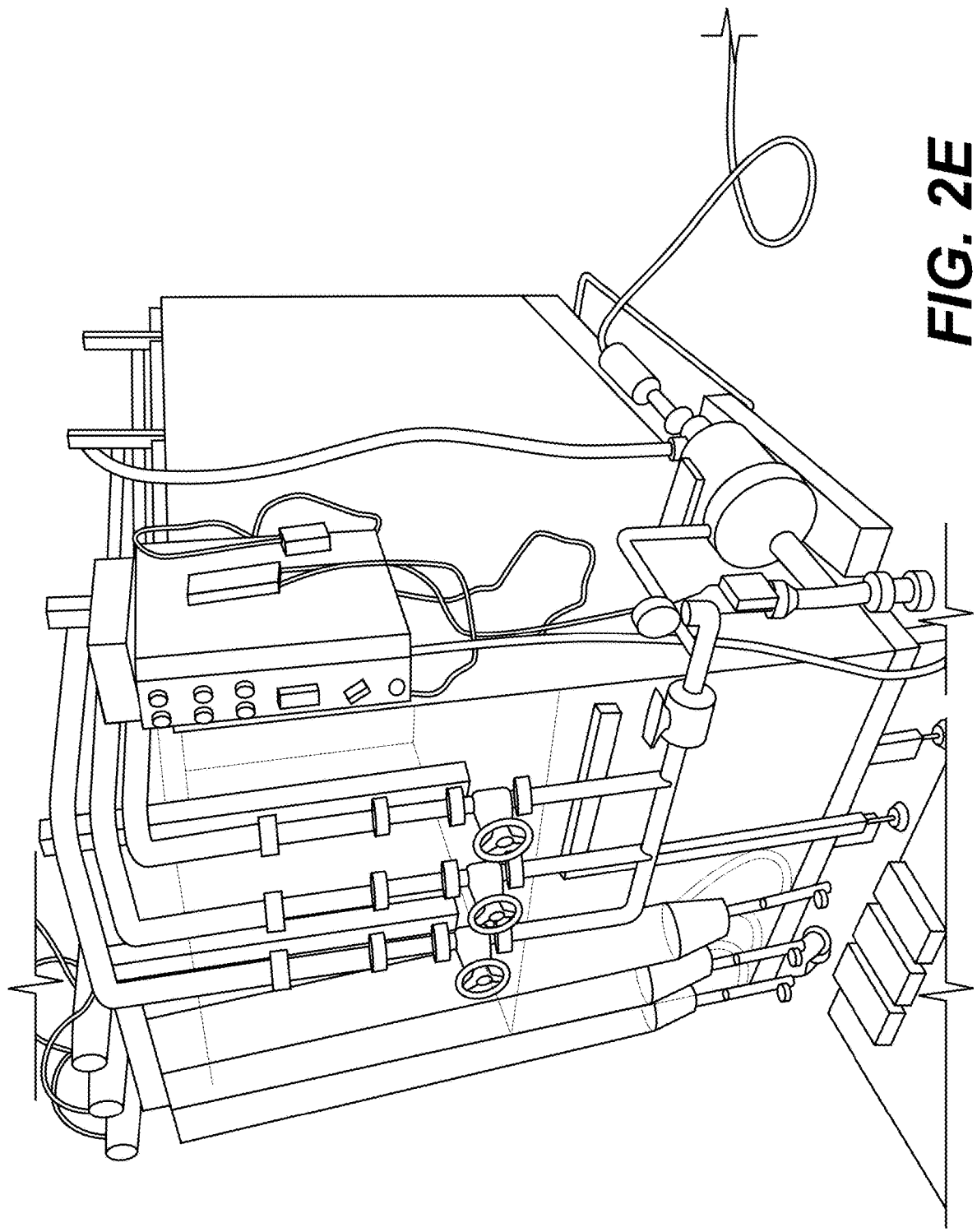

FIGS. 2A-F are diagrams and depictions of the multi jet CPLJR 102 of FIG. 1B, installed and commissioned in a laboratory environment. FIG. 2A is a schematic diagram of CPLJR 102. FIGS. 2B and 2C are front and end views, respectively. FIGS. 2D and 2E are oblique top and oblique rear views, respectively. FIG. 2F shows details of the soap bubble meters/sensors.

Referring to FIG. 2A, CPLJR 102 includes water tank 211, downcomers 221, 222, 223, with injection supply lines 229, terminating at nozzles 235, 236, 237 located within downcomers 221, 222, 223 or otherwise positioned to inject water (brinewater) into downcomers 221, 222, 223. Outlet 239 permits controlled drainage of tank 211. Also depicted are rotameter 241, wave generation device 245, pump 247, brine solution tank 251, brine mixer pump 253, conductivity sensors 261, 262 connected to respective conductivity analyzers 265, 266. Illumination lamp 268 is provided for observation.

CPLJR 102 is designed similarly to single jet CPLJR 101 but with a few additional features. Tank 211 is significantly larger than that of CPLJR 101 to accommodate measurements from water discharged from the multiple downcomers 221, 222, 223. Referring to FIG. 2B, three bubble traps 271, 272, 273 are placed next to respective bubble meters 275, 276, 277 to trap the bubbles coming through tubing 279. Bubble generator 281 is used to generate bubbles. An additional water inlet supply 291 is provided to tank 211 to speed up the water filling process. Multiple conductivity sensors 293 and multiple oxygen tanks 295 are connected to analyzer 298, to provide accurate measurement readings during a test run.

In the described implementation, automated bubble meters 275, 276, 277 are used. Bubble meters 275, 276, 277 are used to measure the entrained air/gas from the ambient surroundings (or any source) going into the liquid, utilizing soap bubbles. Bubble meters 275, 276, 277 are used to measure the entrained air/gas from the ambient surroundings (or any source) going into the liquid utilizing soap bubbles. Bubble meters are used for at least a subset of the PJLRs. In one non-limiting configuration, the number of automated bubble meters 275, 276, 277 match the number of diffusers. The measurement of the bubbles are achieved in a reliable and consistent fashion by the use of automated bubble meters for the respective PJLRs.

While downcomers 221, 222, 223 are described, any suitable water injection system can be used. Therefore, downcomers 221, 222, 223, as described herein can refer to any water injector or water injection system. The downcomers 221, 222, 223 provide a convenient gravity feed and are likely to simulate actual full-scale plant conditions. Pumped water and the like can also be used and can provide the desired test conditions.

Wave generation device 245 and bubble generator 281 are used to generate waves mimicking ambient seawater, allowing engineers to investigate the influence of such waves on the system performance and the multi-jet array used in CPLJR 102. Bubble generator 281 can be used to automatically generate bubbles or soap bubbles to measure air flow inside the bubble.

FIG. 2F shows details of the soap bubble meters/sensors. The bubble meter is made of an acrylic cylinder to measure the amount of air entrained by the water jet ejecting from the nozzle. The bubble meter uses soap mixture to measure the entrained air. As the entrained air enters the bubble meter it carries a soap bubble in a vertical direction. The distance traveled by the soap bubble over the time gives the air velocity and hence the air volumetric flow rate. The volumetric air entrainment rate, $Q_a$, is measured using a soap bubble meter, which provides negligible resistance to the flow. In the prototype, the soap bubble meter comprised a cylindrical tube with an inner diameter of 73 mm and a length of 1000 mm. The soap bubbles were generated inside the bubble meter using a solution made of 10% household detergent and 5% glycerin, with the remainder being water.

Figure 3:
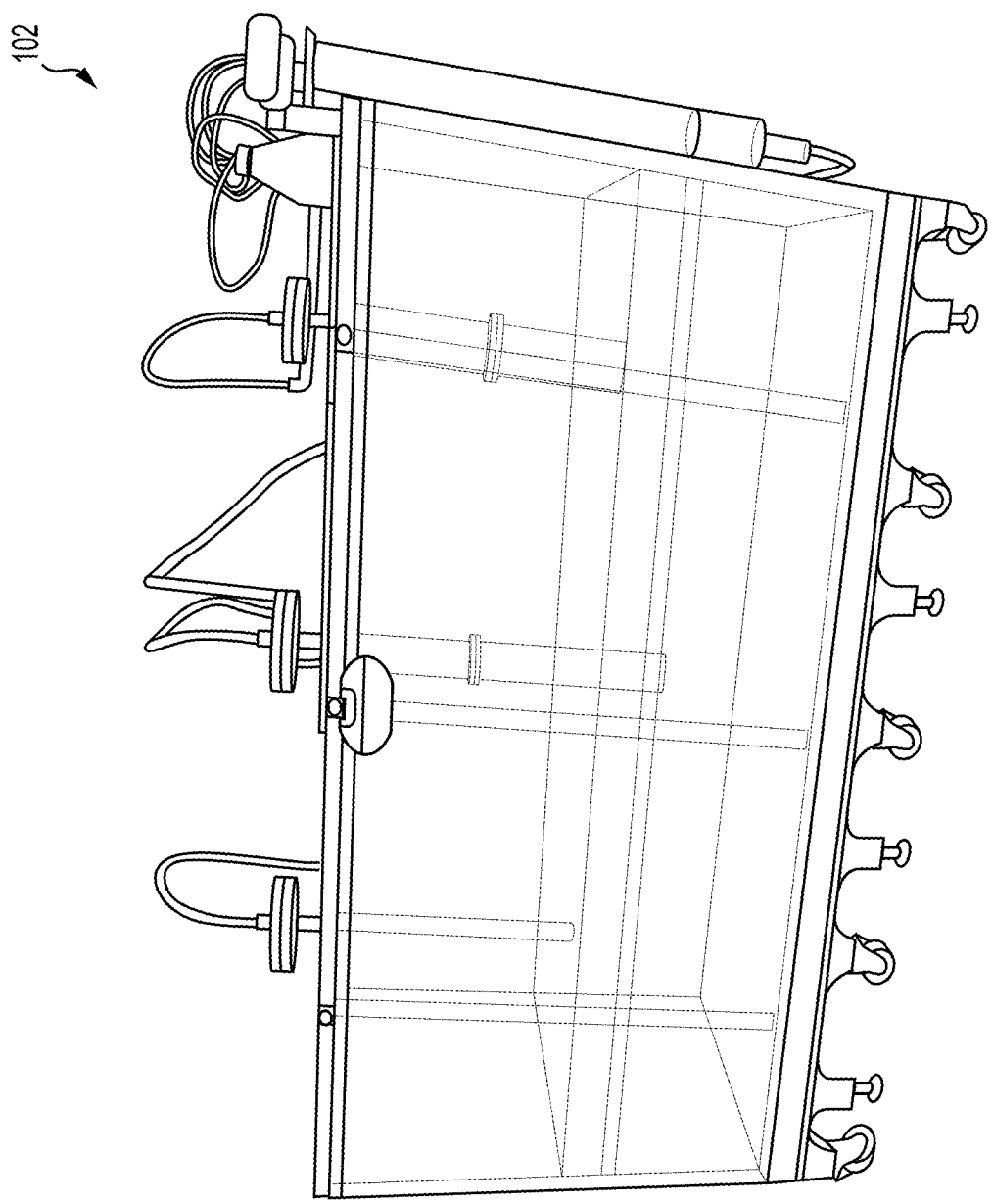
FIG. 3 is an image of CPLJR as used in a laboratory environment.

FIG. 3 is an image of CPLJR 102, with illumination and a depiction of a desalinization plant for perspective. The illumination also provides a visual indication of the water flow.

Figure 4A:
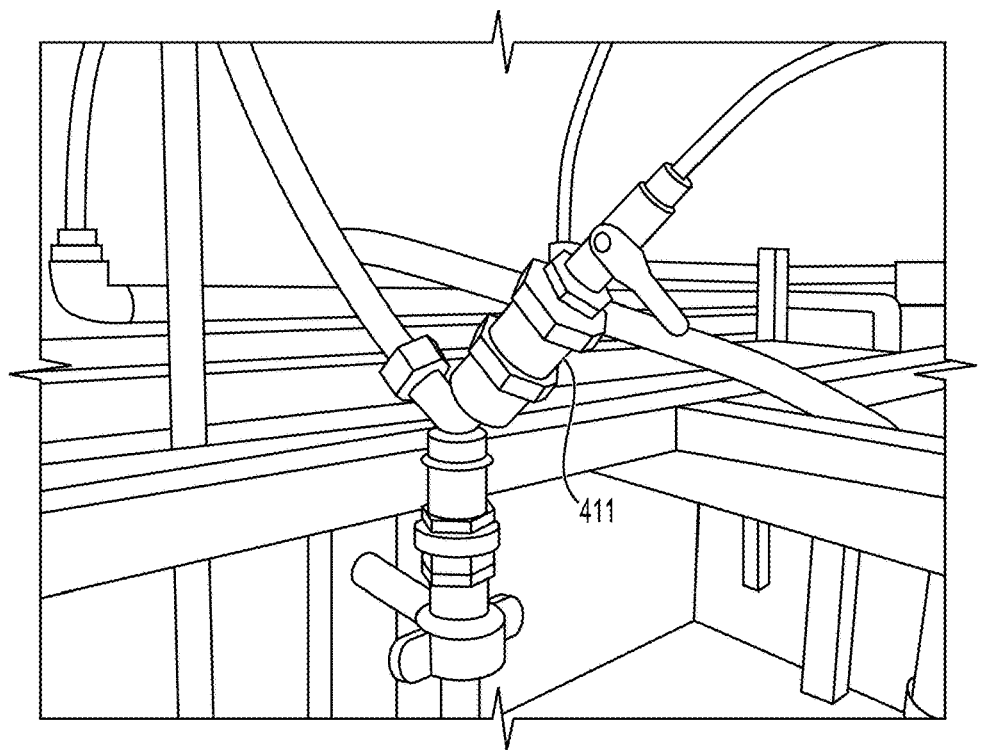
FIGS. 4A and 4B are schematic diagrams showing a dye injection system.
Figure 4B:
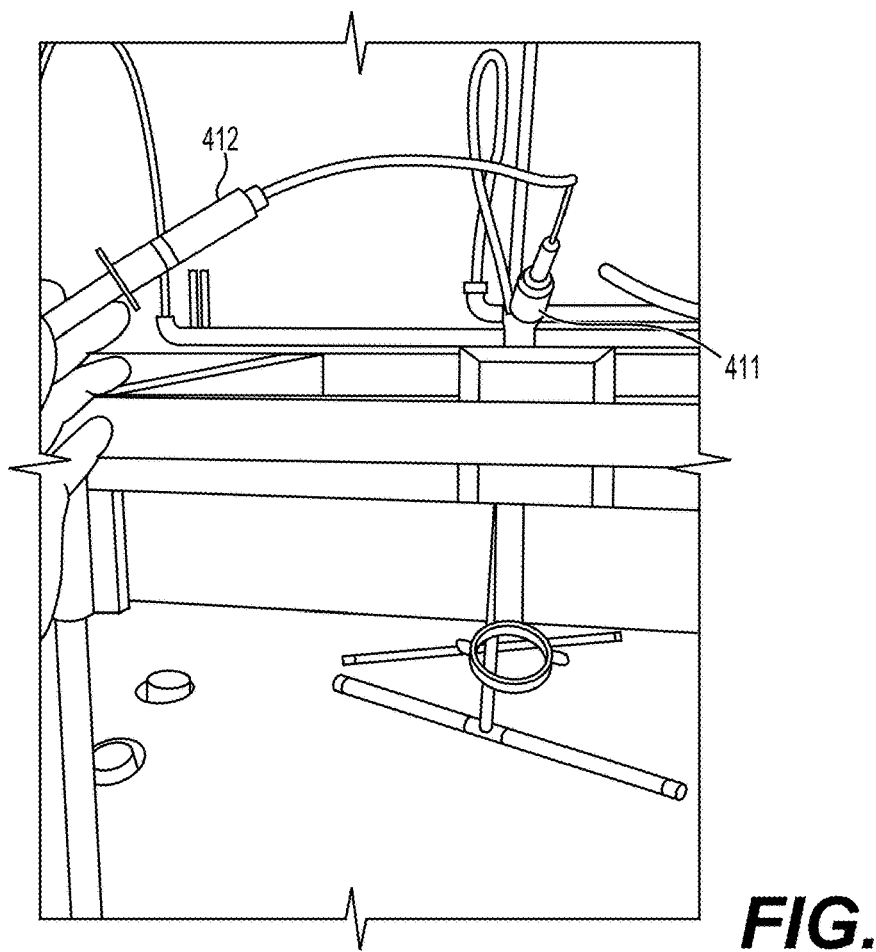
Figure 5A:
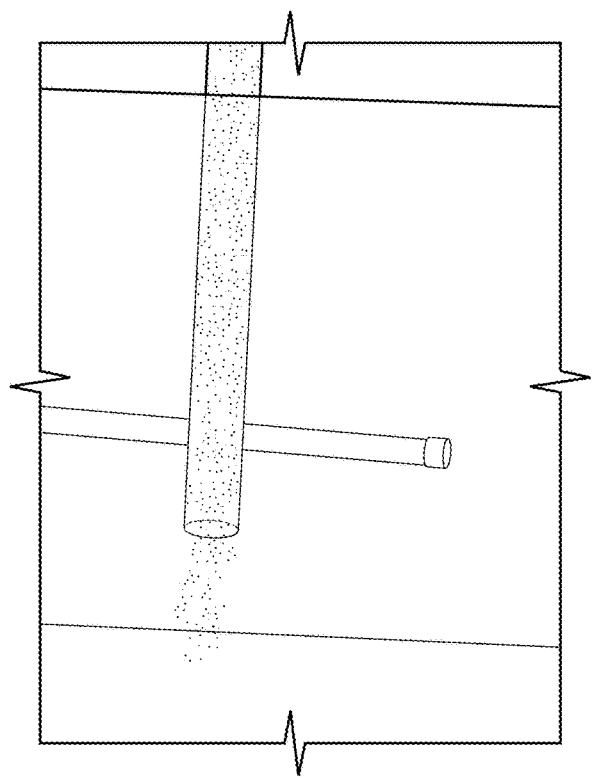
FIGS. 5A-D show a confined JLJR system at specified operating conditions.
Figure 5B:
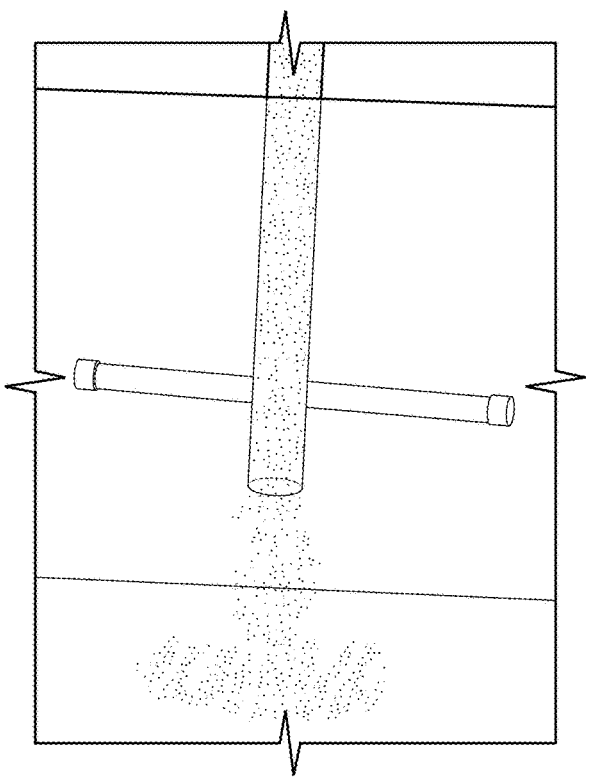
Figure 5C:
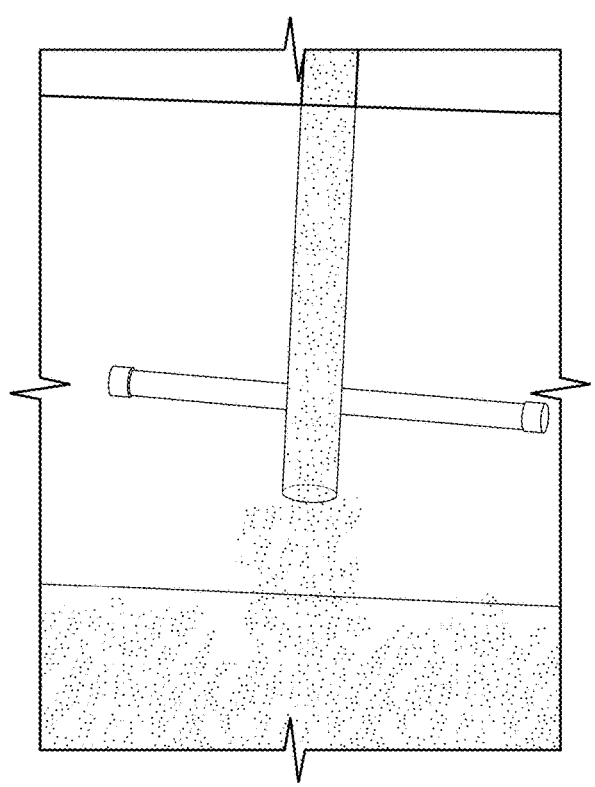
Figure 5D:
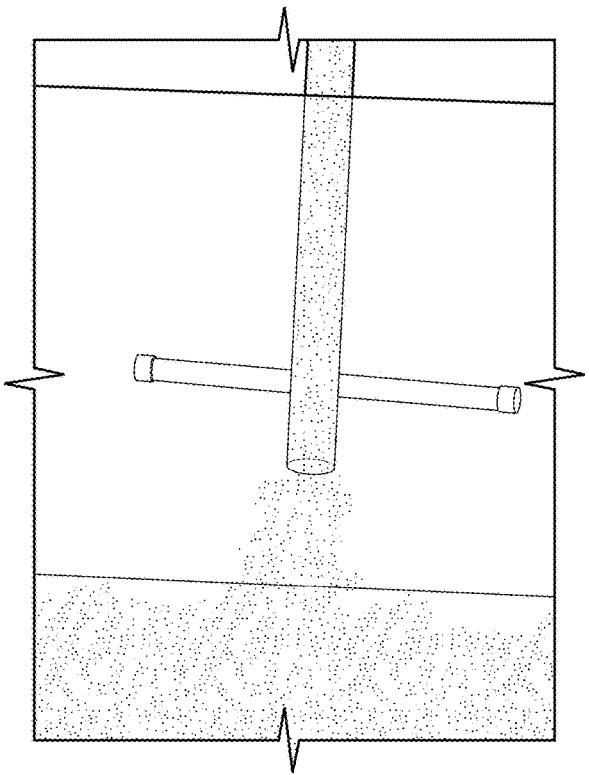

FIGS. 4A and 4B are schematic diagrams showing a dye injecting system. Depicted are dye injection unit 411 and syringe 413. The dye is introduced at nozzles 235, 236, 237 (FIG. 2A) to allow the injection of dye into the incoming jet flow.

FIGS. 5A-D, 6A-C and 7A-C are images depicting experiments carried out using the dye injection. FIGS. 5A-D show a confined JLJR system. FIGS. 6A-C and 7A-C show unconfined JLJR systems.

Confined and unconfined PLJR experiments were carried out employing CPLJR 102, as the multi-jet pilot tank, using dye. A salt solution with concentration of 40 psu, higher than that of the receiving pool, was pumped into the pilot tank (tank 251) and a dye was added in the brine solution through the injection point, to clearly show the trajectory of the brine-bubble two-phase mixture below the receiving pool after the jet impingement.

FIGS. 5A-D show confined jet experiments carried out at the following operating conditions: QL=20 LPM, Del S=40 psu, Lj=40 cm, Dn=8.1 mm for a confined JLJR system. For a confined PLJR system, most of the brine solution plunges downward with a small portion of the brine ascending with the bubbles as they leave the bottom of downcomers 221, 222, 223. This is as expected since long downcomers (downcomers 221, 222, 223) hinder the direct mixing with the surrounding liquid until the mixture ejects from the end of the downcomers. Most of the dye gets radially dispersed at the tank base. This cannot be generalized for all of the downcomers 221, 222, 223, as they vary in lengths, and hence more investigation may be performed to verify such phenomena.

Figure 6A:
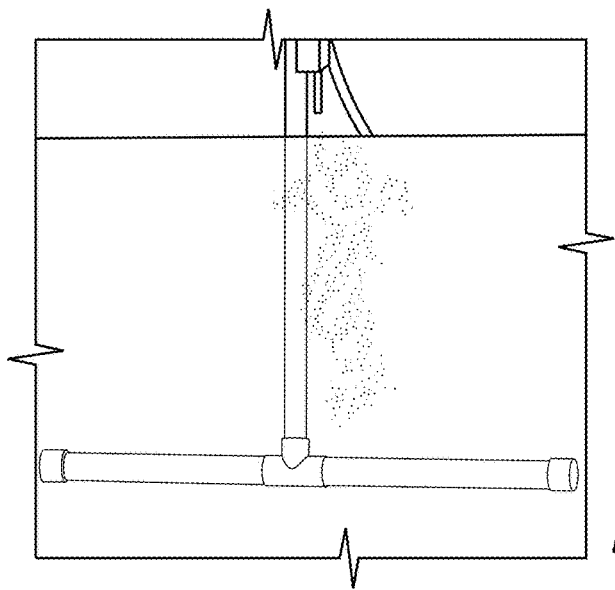
FIGS. 6A-C show an unconfined JLJR system at specified operating conditions.
Figure 6B:
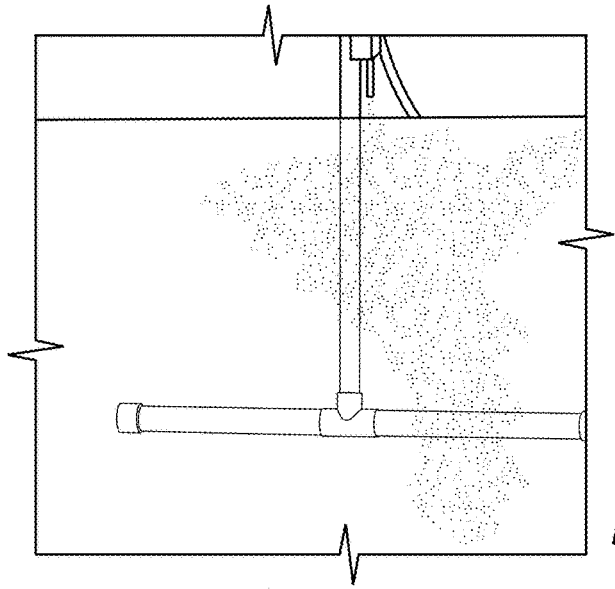
Figure 6C:
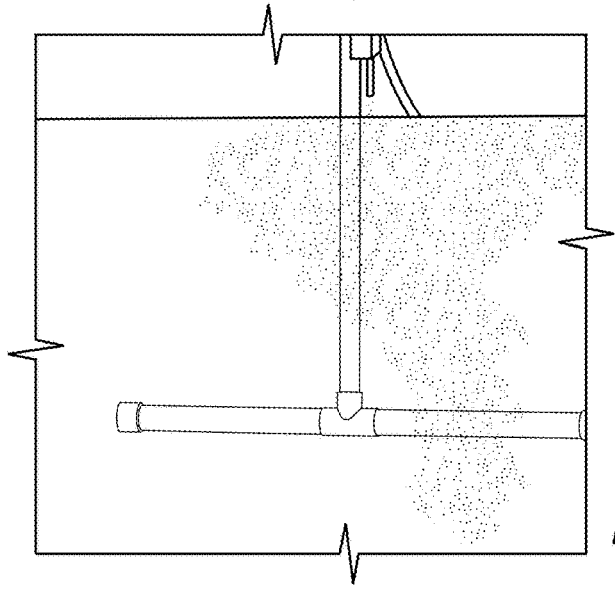
Figure 7A:
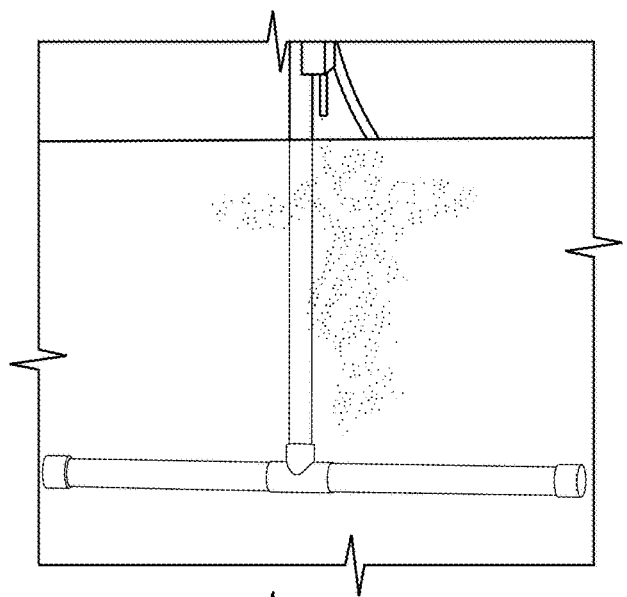
FIGS. 7A-C show an unconfined JLJR system at a different set of specified operating conditions.
Figure 7B:
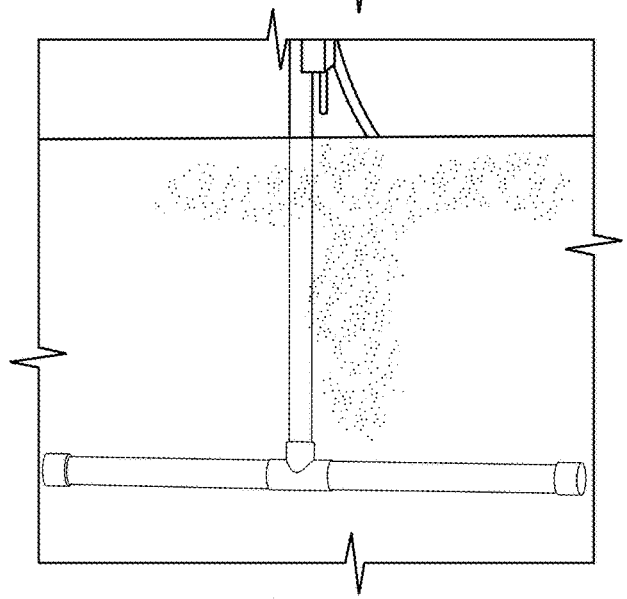
Figure 7C:
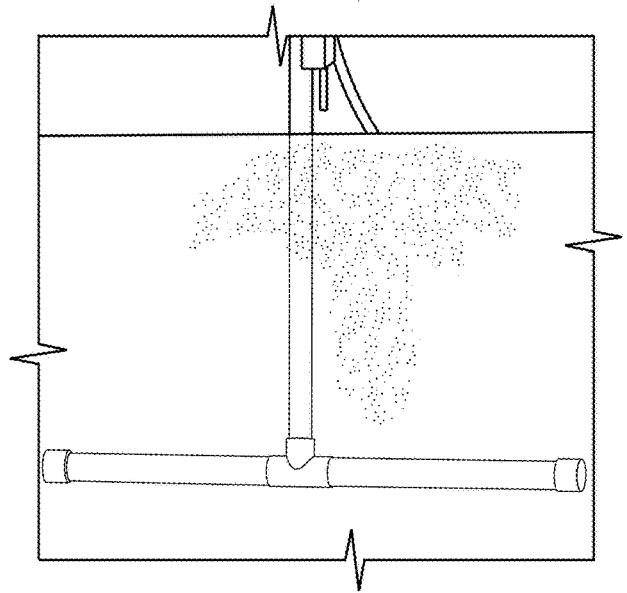

Unconfined PLJR system testing is shown in the depictions of FIGS. 6A-C and 7A-C. FIGS. 6A-C show unconfined jet experiments carried out at the following operating conditions: QL=20 LPM, Del S=40 psu, Lj=40 cm, Dn=8.1 mm. FIGS. 7A-C show unconfined jet experiments carried out at the following operating conditions: QL=20 LPM, Del S=40 psu, Lj=40 cm, Dn=8.1 mm.

For the unconfined PLJR system, the depictions of FIGS. 6A-C and 7A-C clearly show that the incoming brine mixes with the surrounding liquid at early stages limiting the brine-bubble mixture depth causing it to ascend with the bubbles (preventing it from settling at the bottom) and then spreads radially along the receiving pool surface.

CLOSING STATEMENT

The describe examples are of a specific developmental prototype. The details, such as numbers of downcomers 221, 222, 223, particular configurations of the components and the specific techniques of operation are given by way of non-limiting example. It is anticipated that the configuration and technique will be modified in accordance with the anticipated requirements in a given brine discharge environment.

It will be understood that many additional changes in the details, materials, steps and arrangement of parts, which have been herein described and illustrated to explain the nature of the subject matter, may be made by those skilled in the art within the principle and scope of the invention as expressed in the appended claims.

What is claimed is:

1. A Confined Plunging Liquid Jet Reactor (CPLJR) for determining the effect of discharge of an effluent into seawater, comprising:
a tank;
a plurality of water injectors for supplying sample effluents into the tank at multiple locations;
a pump to provide the supplied effluents;
a water movement generator capable of simulating environmental movement of water in the tank;
a plurality of bubble measurement sensors capable of measuring bubbles in the supplied effluents supplied by at least a subset of the water injectors, with respective ones of the bubble measurement sensors sensing bubbles associated with individual ones of the subset of water injectors; and
a plurality of oxygen sensors for measuring oxygenation at different locations or levels in the tank.

2. The CPLJR of claim 1, wherein the tank and water injectors have a configuration for simulation of brine injection into seawater.

3. The CPLJR of claim 1, further comprising:
the water injectors comprising:
a plurality of downcomers; and
injection supply lines, terminating at nozzles positioned to inject water into respective ones of the downcomers, with respective ones of the bubble sensors located upstream of the nozzles.

4. The CPLJR of claim 1, further comprising:
the water injectors comprising:
a plurality of downcomers, the water injectors and downcomers operating as diffusers; and
injection supply lines, terminating at nozzles positioned to inject water into respective ones of the downcomers, with respective ones of the bubble sensors located upstream of the nozzles,
wherein the tank and water injectors have a configuration for simulation of brine injection into seawater.

5. The CPLJR of claim 4, further comprising:
a dye injecting system comprising dye injection units capable of introducing dye into at least a subset of the nozzles.

6. The CPLJR of claim 4, further comprising:
bubble meters associated with the bubble sensors to measure entrained air upstream of the nozzles, the bubble meters measuring entrained air or gas in the liquid, utilizing a surface tension enhancement substance, wherein the number of automated bubble meters match the number of diffusers; and
a plurality of bubble traps located downstream the respective bubble meters and upstream the respective nozzles to trap the bubble that is used to measure the entrained air.

7. The CPLJR of claim 1, further comprising:
a dye injecting system comprising dye injection units capable of introducing dye into at least a subset of the nozzles.

8. The CPLJR of claim 1, further comprising:
a dye injecting system comprising dye injection units capable of introducing dye into at least a subset of the nozzles.

9. A method of determining the effect of discharge of an effluent into seawater using a Confined Plunging Liquid Jet Reactor (CPLJR), the method comprising:
providing a tank;
using a water injector system comprising water injectors for supplying sample effluents into the tank at multiple locations;
simulating environmental movement of water in the tank;
measuring bubbles in the supplied effluents supplied by at least a subset of the water injectors by sensing bubbles associated with individual ones of the subset of water injectors in the subset of the water injectors; and
measuring oxygenation at different locations or levels in the tank.

10. The method of claim 9, wherein the tank and water injectors have a configuration for simulation of brine injection into seawater.

11. The method of claim 9, further comprising:
injecting the water through nozzles within respective ones of a plurality of downcomers; and
using a bubble measurement system to measure entrained air movement upstream of at individual ones of least a subset the nozzles,
wherein the tank and water injectors have a configuration for simulation of brine injection into seawater.

12. The method of claim 11, further comprising:
introducing dye into at least a subset of the nozzles.

13. Confined Plunging Liquid Jet Reactor (CPLJR) for determining the effect of brine injection into seawater, comprising:
a tank;
means for supplying sample effluents into the tank at multiple injection sites within the tank;
a water movement generator capable of simulating environmental movement of water in the tank;
bubble measurement means capable of measuring bubbles to at least a subset of the multiple injection sites, comprising respective\bubble measurement sensors sensing bubbles associated with individual ones of the subset of the multiple injection sites; and
a plurality of oxygen sensors for measuring oxygenation at different locations or levels in the tank.

14. The CPLJR of claim 13, further comprising:
a dye injecting system comprising dye injection units capable of introducing dye into at least a subset of the nozzles;
bubble sensing means capable of providing indications of entrained air or gas in liquid entering the multiple injection sites, utilizing a surface tension enhancement substance; and
bubble traps to trap the bubble that is used to measure the entrained air.

* * * * *